(12) United States Patent
Yared et al.

(10) Patent No.: US 11,903,675 B2
(45) Date of Patent: Feb. 20, 2024

(54) SYSTEMS, METHODS, AND APPARATUS FOR IMAGING OF DIFFUSE MEDIA FEATURING CROSS-MODALITY WEIGHTING OF FLUORESCENT AND BIOLUMINESCENT SOURCES

(71) Applicant: VisEn Medical, Inc., Waltham, MA (US)

(72) Inventors: Wael Yared, Lexington, MA (US); Joshua Kempner, Reading, MA (US); Jorge Ripoll Lorenzo, Madrid (ES); Alicia Arranz, Madrid (ES)

(73) Assignee: VisEn Medical, Inc., Waltham, MA (US)

( * ) Notice: Subject to any disclaimer, the term of this patent is extended or adjusted under 35 U.S.C. 154(b) by 789 days.

(21) Appl. No.: 16/928,125

(22) Filed: Jul. 14, 2020

(65) Prior Publication Data
US 2020/0337559 A1 Oct. 29, 2020

Related U.S. Application Data

(62) Division of application No. 14/054,651, filed on Oct. 15, 2013, now Pat. No. 10,743,768.
(Continued)

(51) Int. Cl.
*A61B 5/00* (2006.01)
*A61K 49/00* (2006.01)
(Continued)

(52) U.S. Cl.
CPC .......... *A61B 5/0071* (2013.01); *A61B 5/0073* (2013.01); *A61B 5/061* (2013.01);
(Continued)

(58) Field of Classification Search
None
See application file for complete search history.

(56) References Cited

U.S. PATENT DOCUMENTS

| 4,981,977 A | 1/1991 | Southwick et al. |
| 5,268,486 A | 12/1993 | Waggoner et al. |

(Continued)

FOREIGN PATENT DOCUMENTS

| EP | 0988060 A2 | 3/2000 |
| EP | 1065250 A1 | 1/2001 |

(Continued)

OTHER PUBLICATIONS

Apr. 13, 2020—(US) Notice of Allowance—U.S. Appl. No. 14/054,651.
(Continued)

*Primary Examiner* — Lina Cordero
(74) *Attorney, Agent, or Firm* — Banner & Witcoff, Ltd.

(57) ABSTRACT

In certain embodiments, the invention relates to systems and methods for in vivo tomographic imaging of fluorescent probes and/or bioluminescent reporters, wherein a fluorescent probe and a bioluminescent reporter are spatially co-localized (e.g., located at distances equivalent to or smaller than the scattering mean free path of light) in a diffusive medium (e.g., biological tissue). Measurements obtained from bioluminescent and fluorescent modalities are combined per methods described herein.

20 Claims, 6 Drawing Sheets

Related U.S. Application Data

(60) Provisional application No. 61/714,198, filed on Oct. 15, 2012.

(51) Int. Cl.
*A61B 5/06* (2006.01)
*G01N 21/64* (2006.01)
*G01N 21/17* (2006.01)

(52) U.S. Cl.
CPC ........ *A61B 5/7214* (2013.01); *A61K 49/0017* (2013.01); *G01N 21/6456* (2013.01); *G01N 21/6486* (2013.01); *G01N 2021/1787* (2013.01)

(56) References Cited

U.S. PATENT DOCUMENTS

| | | |
|---|---|---|
| 5,486,616 A | 1/1996 | Waggoner et al. |
| 5,569,587 A | 10/1996 | Waggoner |
| 5,569,766 A | 10/1996 | Waggoner et al. |
| 5,627,027 A | 5/1997 | Waggoner |
| 5,808,044 A | 9/1998 | Brush et al. |
| 5,877,310 A | 3/1999 | Reddington et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,127,134 A | 10/2000 | Minden et al. |
| 6,130,094 A | 10/2000 | Waggoner et al. |
| 6,133,445 A | 10/2000 | Waggoner et al. |
| 6,136,612 A | 10/2000 | Della Ciana et al. |
| 6,448,008 B1 | 9/2002 | Caputo et al. |
| 6,534,041 B1 | 3/2003 | Licha et al. |
| 6,615,063 B1 | 9/2003 | Ntziachristos et al. |
| 6,747,159 B2 | 6/2004 | Caputo et al. |
| 7,383,076 B2 | 6/2008 | Ntziachristos et al. |
| 7,445,767 B2 | 11/2008 | Licha et al. |
| 7,473,415 B2 | 1/2009 | Kawakami et al. |
| 7,488,468 B1 | 2/2009 | Miwa et al. |
| 7,547,721 B1 | 6/2009 | Miwa et al. |
| 7,647,091 B2 | 1/2010 | Ntziachristos et al. |
| 7,983,740 B2 | 7/2011 | Culver et al. |
| 8,170,651 B2 | 5/2012 | Ripoll Lorenzo et al. |
| 2004/0015062 A1 | 1/2004 | Ntziachristos et al. |
| 2007/0238957 A1 | 10/2007 | Yared |
| 2008/0312540 A1* | 12/2008 | Ntziachristos ....... A61B 5/0084 600/478 |
| 2010/0078576 A1 | 4/2010 | Ntziachristos et al. |
| 2011/0049384 A1 | 3/2011 | Yared et al. |
| 2011/0060211 A1 | 3/2011 | Lorenzo et al. |
| 2011/0071388 A1 | 3/2011 | Yared et al. |
| 2011/0087111 A1 | 4/2011 | Ntziachristos |
| 2011/0184277 A1 | 7/2011 | Ripoll Lorenzo et al. |

FOREIGN PATENT DOCUMENTS

| | | |
|---|---|---|
| EP | 1113822 A1 | 7/2001 |
| EP | 1181940 A2 | 2/2002 |
| EP | 1237583 A1 | 9/2002 |
| EP | 0796111 B1 | 4/2003 |
| EP | 1480683 A2 | 12/2004 |
| EP | 1679082 A1 | 7/2006 |
| EP | 1833513 A1 | 9/2007 |
| NO | 2011025950 A2 | 3/2011 |
| WO | 96/17628 A1 | 6/1996 |
| WO | 97/40104 A1 | 10/1997 |
| WO | 98/47538 A2 | 10/1998 |
| WO | 99/51702 A1 | 10/1999 |
| WO | 00/16810 A1 | 3/2000 |
| WO | 01/21624 A1 | 3/2001 |
| WO | 01/43781 A1 | 6/2001 |
| WO | 03/074091 A2 | 9/2003 |
| WO | 2004008123 A1 | 1/2004 |
| WO | 2006062895 A2 | 6/2006 |
| WO | 2006063246 A1 | 6/2006 |
| WO | 06/072580 A1 | 7/2006 |

OTHER PUBLICATIONS

Achilefu et al., Novel Receptor-Targeted Fluorescent Contrast Agents for In Vivo Tumor Imaging, Investigative Radiology, Aug. 2000—vol. 35—Issue 8, pp. 479-485 (39 pages).

Baird et al., Biochemistry, mutagenesis, and oligomerization of DsRed, a red fluorescent protein from coral, Proc. Nat. Acad. Sci., Oct. 24, 2000, vol. 97, No. 22, 11984-11989, 6 pages.

Ballou et al., Tumor Detection and Visualization Using Cyanine Fluorochrome-Labeled Antibodies, Biotechnol. Prog. 1997, 13, 649-658.

Becker et al., Receptor-targeted optical imaging of tumors with near-infrared fluorescent ligands, Nature Biotechnology, vol. 19, Apr. 2001, pp. 327-331.

Bremer et al., In vivo molecular target assessment of matrix metalloproteinase inhibition, Nature Medicine, vol. 7, No. 6, Jun. 2001, pp. 743-748.

Bugaj et al., Novel fluorescent contrast agents for optical imaging of in vivo tumors based on a receptor-targeted dye-peptide conjugate platform, Journal of Biomedical Optics, Apr. 2001, vol. 6 No. 2, pp. 122-133.

Campbell et al., A monomeric red fluorescent protein, Proc. Nat. Acad. Sci., Jun. 11, 2002 Vol. 99, No. 12, 7877-7882.

Campo et al., Polymeric Photosensitizer Prodrugs for Photodynamic Therapy, Photochem. Photobiol., 2007, 83:958-965.

Cubitt et al., Understanding, improving and using green fluorescent proteins, Trends Biochem Sci., Nov. 1995, 20:448-455.

Davis, S. C. et al., Magnetic resonance-coupled fluorescence tomography scanner for molecular imaging of tissue, Review of Scientific Instruments, AIP, Melville, NY, US, 79(6):643202-1-10 (2008).

Fischer, R. et al., Basic Optical and Optical Systems Specifications, Optical System Design, 2nd Ed. N.P.:McGrawh-Hill, p. 17 (2008).

Giepmans et al., The Fluorescent Toolbox for Assessing Protein Location and Function, Science, Apr. 14, 2006, vol. 312, pp. 217-224.

Guven, M. et al, Diffuse optical tomography with a priori anatomical information, Physics in Medicine and Biology, 50(12):2837-2858 (2005).

Hecht, J., Fiber Lasers: Fiber lasers: The state of the art, 11 pages, (2012), retrieved Jun. 25, 2017 from <http://www.laserfocusworld.com/articles/print/volume-48/issue-04/features/the-state-of-the-art.html>.

Heikal et al., Mollecular spectroscopy and dynamics of intrinsically fluorescent proteins: coral; red (dsRed) and yellow (Citrine), Proc. Nat. Acad. Sci., Oct. 24, 2000, vol. 97, No. 22, pp. 11996-12001.

Heim et al., Engineering green fluorescent protein for improved brightness, longer wavelengths and fluorescence resonance energy transfer, Curr. Biol., 1996, 6:178-182.

Heim et al., Wavelength mutations and prostranslational autoxidation of green fluorescent protein, Proc. Nat. Acad. Sci., Dec. 1994, vol. 91 pp. 12501-12504.

Hwang et al, A Multimode Optical Imaging System for Preclinical Applicatons: Technology Development, Multiscale Imaging, and Chemotherapy Assessment, Molecular Imaging and Bioloqv, vol. 14, No. 4, August 27, 2011, 12 paqes.

Noue et al, In Vivo Fluorescence Imaging of the Reticuloendothelial System Using Quantum Dots in Combination with Bioluminescent Tumour Monitoring, Eur J. Nucl Med Mol Imaging, vol. 34, No. 12, Sep. 21, 2007, 9 Pages.

International Search Report, PCT/US2013/065107, dated Dec. 16, 2013, 5 pages.

Lackowicz, Principles of Fluorescence Spectroscopy Third Edition, Springer Science + Business Media LLC, 960 pages.

Mohajerani, P. et al., FMT-PCCT: Hybrid Fluorescence Molecular Tomography—X-Ray Phase-Contrast CT Imaging of Mouse Models, IEEE Transactions on Medical Imaging, 33(7):1434-1446 (2014).

(56) References Cited

OTHER PUBLICATIONS

Neri et al., Targeting by affinity-matured recombinant antibody fragments of an angiogenesis; associated fibronectin isoform, Nature Biotechnology, vol. 15, Nov. 1997, pp. 1271-1275.

Ntziachristos, V., Fluorescence Molecular Imaging, Annu. Rev. Biomed. Eng., 8:1-33 (2006).

Ozmen et al, Infrared fluorescence sensing of submicromolar calcium: pushing the limits of photoinduced electron transfer, Tetrahedron Letters 41 (2000) pp. 9185-9188.

Saggau, P., New Methods and uses for fast optical scanning, Curr. Opin. Neurobiol., 16(5):543-550 (2006).

Shaner et al., A Guide to Choosing Fluorescent Proteins, Nature Methods, vol. 2, No. 12, Dec. 2005, pp. 905-909.

Shaner et al., Improved monomeric red, orange and yellow fluorescent proteins derived from *Discoma* sp red fluorescent protein, Nat. Biotech, Dec. 2005, vol. 22, pp. 1567-1572.

Shi, L. et al, Transmission in near-infrared optical windows for deep brain imaging, J Biophotonics, 9(1-2):38-43 (2016).

Tsien, The green fluorescent protein, Ann. Rev. Biochem., 1998, 67:509-544.

Tyagi et al, Wavelength-shifting molecular beacons, Nature Biotechnology, vol. 18, Nov. 2000, pp. 1191-1196.

Tyagi et al., Multicolor molecular beacons for allele discrimination, Nature Biotechnology, vol. 16, Jan. 1998, pp. 49-53.

Weissleder et al., In vivo imaging of tumors with protease-activated near-infrared fluorescent probes, Nature Biotechnology, vol. Apr. 17, 1999, pp. 375-378.

Wikipedia, Fiber Laser, 4 pages, retrieved from <https://en.wikipedia.org/wiki/Fiber_laser>, Jun. 25, 2017.

Written Opinion, PCT/US2013/065107, dated Dec. 16, 2013, 8 pages.

Zhang et al., Creating new fluorescent probes for cell biology, Nat. Rev. Mol. Biol., Cecember 2002, 3:906-918.

\* cited by examiner

True depth location of Bio-Fluo tandem = 1.45 cm
Non-specific fluorophore of the same concentration and brightness as the Bio-Fluo signal.

SYSTEMS, METHODS, AND APPARATUS FOR IMAGING OF DIFFUSE MEDIA FEATURING CROSS-MODALITY WEIGHTING OF FLUORESCENT AND BIOLUMINESCENT SOURCES

CROSS REFERENCE TO RELATED APPLICATIONS

This application claims priority to U.S. patent application Ser. No. 14/054,651, filed Oct. 15, 2013, and having the same title, which in turn claims priority to and the benefit of, U.S. Provisional Patent Application No. 61/714,198, filed Oct. 15, 2012, each of which is hereby incorporated by reference in their entirety.

FIELD

The invention relates generally to in vivo imaging systems and methods. More particularly, in certain embodiments, the invention relates to a tomographic imaging system employing co-located fluorescent and bioluminescent sources.

BACKGROUND

Imaging in diffusive media has become an attractive field of research mainly due to its applications in biology and medicine, showing great potential in, for example, cancer research, drug development, inflammation and molecular biology. With the development of highly specific activatable fluorescent probes, a new way of obtaining information at the molecular level in vivo has been made possible. Due to the inherent scattering present in tissues in the optical wavelengths, light is multiply scattered in tissue and its original direction of propagation is randomized after what is termed the scattering mean free path, lsc, a distance which represents the density and efficiency of scattering of the different constituents of tissue. Even though images of fluorescent or bioluminescent emission from tissues might be recorded, due to the scattering present, there is a non-linear relation of these images with the concentration, size and position of the fluorescent probes or bioluminescent reporters, resulting in what is termed an ill-posed problem. Recently developed methods and systems make use of tomographic approaches by introducing a spatial dependence of fluorescence on the excitation and appropriate modeling of light propagation in tissues through the diffusion approximation to alleviate this ill-posedness, enabling the recovery of the spatial distribution of the concentration of fluorescence with a resolution on the order of the scattering mean free path (lsc) or better. In an ideal situation, the sensitivity of these tomographic techniques would depend only on the detector efficiency and probe brightness together with the absorption present in tissue, assuming it is possible to completely block the excitation light when measuring fluorescence. In this ideal case, the sensitivity could be increased by augmenting the laser power since the emitted and excitation intensities are proportional to one another, at least for powers acceptable for small animal imaging, which ensure that no appreciable heating occurs in tissue.

However, the reality of an in vivo measurement is quite different. Due to the excitation of surrounding auto-fluorescence always present in tissue, the sensitivity of a system is strongly dependent on the ability to distinguish the specific signal due to the fluorescent probe from the non-specific signal of the surrounding auto-fluorescence. This problem becomes more pronounced when exciting in reflection mode, since the greater auto-fluorescent contribution would be from the tissue sections closest to the camera. In practice, the sensitivity of the tomographic data, or in general any collection of fluorescent data, is determined by the level of auto-fluorescence when compared to the specific signal. This issue is overcome to some extent by using far-red or near infra-red (NIR) fluorescence signals, since tissue auto-fluorescence is slightly reduced in this part of the spectrum, with the added advantage that tissue presents lower absorption properties in this part of the spectrum. This is the case when using fluorescent probes that emit in the far-red or near infra-red part of the spectrum, which are activated when a specific molecular activity is present. An advantage of this kind of probes is that they provide a high signal-to-noise ratio. However, in most practical instances, the amount of signal that can be detected depends on how much specific signal surpasses the surrounding tissue auto-fluorescence.

In order to separate the contribution of the specific from the non-specific signal, the most common approach is to employ multi-spectral measurements, assuming the emission spectrum is known. Even though this approach slightly increases the sensitivity, the problem still remains: at each emission wavelength measured there is an unknown contribution from tissue auto-fluorescence. The weaker the specific signal, the more dominant the effect of auto-fluorescence.

Bioluminescent reporters offer the significant advantage of not requiring an external illumination to place them in an excited state such that they would emit light. Since the excited state is reached though a chemical reaction, the emitted light represents the background-free solution of the imaging problem, akin to the ideal case of fluorescence mentioned in the previous paragraphs. This inherent benefit of bioluminescence also has some drawbacks, specifically in relation to the ill-posed problem mentioned above. Since it is not currently possible to effectively introduce a spatial dependence on the intensity of this emission (whereas this is possible in the case of fluorescence), it is not possible to recover simultaneously the spatial distribution of bioluminescent probe concentration. Thus, because the main goal is to recover the spatial distribution of probe concentration, the ill-posedness of the problem cannot be substantially reduced in the case of bioluminescence as is possible in the case of fluorescence.

There is a need for an optical imaging system in which the low-background and lack of auto-fluorescence of bioluminescent probes can be combined with the specificity, high quantum yield, and the external capability of emission intensity modulation exhibited by fluorescent probes.

SUMMARY

In certain embodiments, the invention relates to systems and methods for in vivo tomographic imaging of fluorescent probes and/or bioluminescent reporters, wherein a fluorescent probe and a bioluminescent reporter are spatially co-localized (e.g., located at distances equivalent to or smaller than the scattering mean free path of light) in a diffusive medium (e.g., biological tissue). Measurements obtained from bioluminescent and fluorescent modalities are combined per methods described herein.

In one aspect, the invention provides a method for imaging a target region of a diffuse object, the method comprising: (a) administering a bioluminescent substrate (and/or chemiluminescent substrate) to the object; (b) detecting bioluminescent (and/or chemiluminescent) light emitted from the object by a bioluminescent reporter in the target region of the object (e.g., using an external detector); (c) administering a probe comprising a fluorescent species (and/or a jointly fluorescent/bioluminescent species) to the object; (d) directing excitation light into the object at multiple locations and/or at multiple angles, thereby exciting the fluorescent species; (e) detecting fluorescent light (e.g., as a function of detector position, excitation light source position, or both), the detected fluorescent light having been emitted by the fluorescent species in the target region of the diffuse object as a result of excitation by the excitation light; (f) detecting excitation light (e.g., as a function of detector position, excitation light source position, or both), the detected excitation light having been transmitted through the region of the diffuse object (transillumination) or having been reflected from the region of the diffuse object (epi-illumination); and (g) processing data corresponding to the detected bioluminescent light, the detected fluorescent light, and the detected excitation light to provide an image of the target region within the diffuse object.

In certain embodiments, the bioluminescent reporter is endogenous. In certain embodiments, the bioluminescent reporter is expressed within the object by a bioluminescent cell line. In certain embodiments, the bioluminescent reporter is exogenously administered. In certain embodiments, the bioluminescent reporter is administered to the object as a component of a tandem bioluminescent-fluorescent probe.

In certain embodiments, following step (c), at least some of the bioluminescent reporter is substantially co-located with at least some of the (fluorescent) probe in the target region of the object. In certain embodiments, following step (c), the bioluminescent reporter is also present in the object at one or more locations that are not substantially co-located with the (fluorescent) probe. In certain embodiments, the probe in step (c) comprises both the fluorescent species and the bioluminescent reporter in tandem with the fluorescent species (e.g., the bioluminescent reporter and fluorescent probe comprises a single construct). In certain embodiments, it is not required that the bioluminescent reporter and the fluorescent species be conjugated or colocalized to within FRET-type distances. Co-located may mean located within a macro-level distance. For example, in certain embodiments, the method may be used even where the bioluminescent reporter and the fluorescent species are separated by a macro-level distance, for example, up to about 1 mm or up to about 2 mm, rather than up to about 5 to 10 nm as in FRET and BRET.

In certain embodiments, the diffuse object comprises living biological tissue (in vivo imaging). In certain embodiments, the diffuse object is a mammal. In certain embodiments, the image of the target region is a tomographic image. In certain embodiments, the method further comprises placing the object within a holder prior to steps (b), (d), (e), and (f). For example, in certain embodiments, the image of the target region is a tomographic image and wherein a surface of the object is at least partially conformed by the holder such that the surface can be characterized by a continuous function (e.g., in Cartesian, polar, or cylindrical coordinates), thereby facilitating tomographic reconstruction.

In certain embodiments, step (b) comprises detecting bioluminescent light using a detector located outside the object. In certain embodiments, step (b) comprises detecting bioluminescent light as a function of detector position. In certain embodiments, step (b) comprises detecting bioluminescent light using a detector in optical contact with the object (e.g., a component of the detector is in physical contact with either the object itself or a transparent surface in physical contact with the object, and/or optical guides, fiber guides, optical matching fluids, and or lenses are used such that optical contact is maintained during detection). In certain embodiments, step (b) comprises detecting bioluminescent light using a detector positioned such that there is a nondiffusive medium (e.g., a layer of air) between the detector and the object. In certain embodiments, step (b) comprises detecting bioluminescent light using an emission filter. In certain embodiments, step (b) comprises detecting bioluminescent light without using an emission filter.

In certain embodiments, the probe in step (c) is a visible or near-infrared fluorescent probe (e.g., a NIRF molecular probe, a red agent, etc.).

In certain embodiments, step (d) comprises directing visible and/or near infrared light into the object. In certain embodiments, step (d) comprises directing a point source of excitation light into the object. In certain embodiments, step (d) comprises simultaneously directing multiple sources of excitation light into the object. In certain embodiments, step (d) comprises directing structured excitation light into the object. In certain embodiments, step (d) comprises directing the excitation light into the object at multiple discrete positions (e.g., an array of positions) and/or at multiple discrete angles (e.g., an array of angles), each instance of directing the excitation light into the object occurring at discrete times.

In certain embodiments, the method comprises performing steps (e) and (f) after each instance of directing excitation light into the object at a discrete position and/or at a discrete angle. In certain embodiments, step (d) comprises directing the excitation light into the object at multiple discrete positions (e.g., an array of positions) and/or at multiple discrete angles (e.g., an array of angles) simultaneously. In certain embodiments, step (d) comprises scanning the excitation light over the object. In certain embodiments, the excitation light detected in step (f) comprises at least one of continuous wave (CW) light, time-resolved (TR) light, and intensity modulated (IM) light.

In certain embodiments, step (e) comprises detecting fluorescent light emitted from the target region of the object using a detector located outside the object. In certain embodiments, step (e) comprises detecting fluorescent light on the same side of the object into which excitation light was directed in step (d) (e.g., epi-illumination). In certain embodiments, step (e) comprises detecting fluorescent light on a side of the object opposite the side into which excitation light was directed in step (d) (e.g., transillumination). In certain embodiments, step (e) comprises detecting fluorescent light emitted from the target region of the object using a detector in optical contact with the object (e.g., a component of the detector is in physical contact with either the object itself or a transparent surface in physical contact with the object, and/or optical guides, fiber guides, optical matching fluids, and or lenses are used such that optical contact is maintained during detection). In certain embodiments, step (e) comprises detecting fluorescent light emitted from the target region of the object using a detector positioned such that there is a nondiffusive medium (e.g., a layer of air) between the detector and the object.

In certain embodiments, step (f) comprises detecting excitation light transmitted through the target region of the object or reflected from the target region of the object using a detector located outside the object. In certain embodiments, step (f) comprises detecting excitation light transmitted through the target region of the object or reflected from the target region of the object using a detector in optical contact with the object (e.g., a component of the detector is in physical contact with either the object itself or a transparent surface in physical contact with the object, and/or optical guides, fiber guides, optical matching fluids, and or lenses are used such that optical contact is maintained during detection). In certain embodiments, step (f) comprises detecting excitation light transmitted through the target region of the object or reflected from the target region of the object using a detector positioned such that there is a nondiffusive medium (e.g., a layer of air) between the detector and the object.

In certain embodiments, step (e) comprises detecting the fluorescent light from multiple projections and/or views. In certain embodiments, step (f) comprises detecting the excitation light from multiple projections and/or views.

In certain embodiments, the target region of the object is a three-dimensional region and step (g) comprises providing a tomographic image that corresponds to the fluorescent species in the three-dimensional target region. In certain embodiments, the tomographic image indicates three-dimensional spatial distribution of the probe (e.g., wherein the probe comprises a fluorescent species and/or a jointly fluorescent/bioluminescent species) within the target region. In certain embodiments, the tomographic image indicates concentration of the probe as a function of position within the target region of the object. In certain embodiments, the tomographic image indicates concentration of the probe as a function of position in three dimensions.

In certain embodiments, the target region of the object is a three-dimensional region and step (g) comprises providing a tomographic image that corresponds to the bioluminescent reporter in the three-dimensional target region. In certain embodiments, the tomographic image indicates three-dimensional spatial distribution of the bioluminescent reporter within the target region. In certain embodiments, the tomographic image indicates concentration of the bioluminescent reporter as a function of position within the target region of the object.

In certain embodiments, the bioluminescent reporter and the fluorescent species have emission spectra that differ.

In certain embodiments, step (g) comprises weighting data corresponding to the detected fluorescent light with data corresponding to the detected bioluminescent light and normalizing data corresponding to the detected fluorescent light with data corresponding to the detected excitation light. In certain embodiments, step (g) comprises weighting data corresponding to the detected fluorescent light with data corresponding to the detected bioluminescent light and then normalizing the resulting weighted data with data corresponding to the detected excitation light, then inverting an associated weight matrix to obtain a/the tomographic image of the fluorescent species in the target region of the object. In certain embodiments, step (g) comprises weighting data corresponding to the detected fluorescent light with data corresponding to the detected bioluminescent light, and weighting an associated weight matrix with data corresponding to the detected bioluminescent light, then inverting the weight matrix to obtain a/the tomographic image of the fluorescent species in the target region of the object. In certain embodiments, step (g) comprises weighting data corresponding to the detected bioluminescent light with data corresponding to the detected fluorescent light normalized with data corresponding to the detected excitation light, then inverting an associated weight matrix to obtain a/the tomographic image of the bioluminescent reporter in the target region of the object.

In certain embodiments, the detecting in step (b) is performed at a different time than the detecting in steps (e) and (f) (e.g., because pharmacokinetics of the probes and the substrate may be different). In certain embodiments, one would time the administration (e.g., injection) of bioluminescent substrate and fluorescent probe such that the imaging of both modalities can be performed in close succession, in order to capture a single "time point". Imaging via the two modes need not occur in exact simultaneity, for example, in an instrument equipped to image in both modalities. It is possible to image using two single-modality instruments that are in proximity such that imaging the object (e.g., a living animal) in one instrument can be performed, and the animal may be shuttled to the second instrument, e.g., within a few minutes. An animal holder may be used, for example, such as that described in U.S. Patent Application Publication No. US 2011/0071388, incorporated herein by reference.

In another aspect, the invention provides a method for imaging a target region of a diffuse object, the method comprising: (a) administering a bioluminescent substrate (and/or chemiluminescent substrate) to the object; (b) detecting bioluminescent (and/or chemiluminescent) light emitted from the object by a bioluminescent reporter in the target region of the object (e.g., using an external detector); (c) administering a probe comprising a fluorescent species (and/or a jointly fluorescent/bioluminescent species) to the object; (d) detecting fluorescent light (e.g., as a function of detector position), the detected fluorescent light having been emitted by the fluorescent species in the target region of the diffuse object as a result of excitation by the bioluminescent light (e.g., bioluminescent stimulation of fluorescence by radiative transfer); and (e) processing data corresponding to the detected bioluminescent light and the detected fluorescent light to provide an image of the target region within the diffuse object.

In certain embodiments, the method further includes directing light (e.g., at an excitation wavelength) into the object and detecting the light having been transmitted through the region of the diffuse object (transillumination) or having been reflected from the region of the diffuse object (epi-illumination) (e.g., to provide a proxy attenuation map), and using data corresponding to the detected light (e.g., using the proxy attenuation map) in step (g) along with the data corresponding to the detected bioluminescent light and the detected fluorescent light to provide the image of the target region within the diffuse object.

In another aspect, the invention provides a system for imaging a target region within a diffuse object, the system comprising: an excitation light source; an optical imaging apparatus configured to direct light from the excitation light source into the diffuse object at multiple locations and/or at multiple angles; one or more detectors, the one or more detectors individually or collectively configured to detect and/or measure (e.g., as a function of detector position, excitation light source position, or both), (i) bioluminescent (and/or chemiluminescent) light emitted from the object, (ii) fluorescent light emitted by a fluorescent species in the target region of the diffuse object as a result of excitation by the excitation light, and (iii) excitation light having been transmitted through the region of the diffuse object or having been reflected from the region of the diffuse object; and a processor configured to process data corresponding to the detected bioluminescent light, the detected fluorescent light, and the detected excitation light to provide an image of the target region within the diffuse object.

In another aspect, the invention provides a system for imaging a target region within a diffuse object, the system comprising: an excitation light source; an optical imaging apparatus configured to direct light from the excitation light source into the diffuse object at multiple locations and/or at multiple angles; one or more detectors, the one or more detectors individually or collectively configured to detect and/or measure (e.g., as a function of detector position, excitation light source position, or both), (i) bioluminescent (and/or chemiluminescent) light emitted from the object, (ii) fluorescent light emitted by a fluorescent species in the target region of the diffuse object as a result of excitation by the excitation light, and (iii) excitation light having been transmitted through the region of the diffuse object or having been reflected from the region of the diffuse object; and a processor configured to process data corresponding to the detected bioluminescent light, the detected fluorescent light, and the detected excitation light to provide an image of the target region within the diffuse object.

In another aspect, the invention provides an apparatus for reconstructing a tomographic representation of a probe within a target region of a diffuse object, the apparatus comprising: a memory that stores code defining a set of instructions; and a processor that executes the instructions thereby to process data corresponding to: (a) establish a forward model of excitation light propagation from an excitation light source to the probe within the target region of the object and of emission light propagation from the probe to a detector using (i) data corresponding to detected fluorescent light from the probe, (ii) data corresponding to detected excitation light having been transmitted through the region of the diffuse object or having been reflected from the region of the diffuse object, and (iii) data corresponding to detected bioluminescent light emitted from a bioluminescent reporter, wherein at least some of the bioluminescent reporter is substantially co-located with at least some of the (fluorescent) probe in the target region of the object, and wherein the forward model is established as a weight matrix; and (b) invert the weight matrix to obtain the tomographic representation of the probe within the target region of the diffuse object.

In another aspect, the invention provides a non-transitory computer readable medium having instructions thereon that, when executed by a processor, cause the processor to: (a) establish a forward model of excitation light propagation from an excitation light source to the probe within the target region of the object and of emission light propagation from the probe to a detector using (i) data corresponding to detected fluorescent light from the probe, (ii) data corresponding to detected excitation light having been transmitted through the region of the diffuse object or having been reflected from the region of the diffuse object, and (iii) data corresponding to detected bioluminescent light emitted from a bioluminescent reporter, wherein at least some of the bioluminescent reporter is substantially co-located with at least some of the (fluorescent) probe in the target region of the object, and wherein the forward model is established as a weight matrix; and (b) invert the weight matrix to obtain the tomographic representation of the probe within the target region of the diffuse object.

In another aspect, the invention provides a method for imaging a target region of a diffuse object, the method comprising: (a) detecting bioluminescent (and/or chemiluminescent) light emitted from the object by a bioluminescent reporter in the target region of the object (e.g., using an external detector); (b) directing excitation light into the object at multiple locations and/or at multiple angles, thereby exciting a fluorescent species of a probe (e.g., a fluorescent probe or a fluorescent/bioluminescent tandem probe) in the target region of the diffuse object; (c) detecting fluorescent light as a function of detector position, excitation light source position, or both, the detected fluorescent light having been emitted by the fluorescent species as a result of excitation by the excitation light; (d) detecting excitation light as a function of detector position, excitation light source position, or both, the detected excitation light having been transmitted through the region of the diffuse object or having been reflected from the region of the diffuse object; and (e) processing data corresponding to the detected bioluminescent light, the detected fluorescent light, and the detected excitation light to provide an image of the target region within the diffuse object.

Elements from embodiments of one aspect of the invention may be used in other aspects of the invention (e.g., elements of claims depending from one independent claim may be used to further specify embodiments of other independent claims). Other features and advantages of the invention will be apparent from the following figures, detailed description, and the claims.

The objects and features of the invention can be better understood with reference to the drawings described below, and the claims. In the drawings, like numerals are used to indicate like parts throughout the various views.

DETAILED DESCRIPTION

Figure 1:
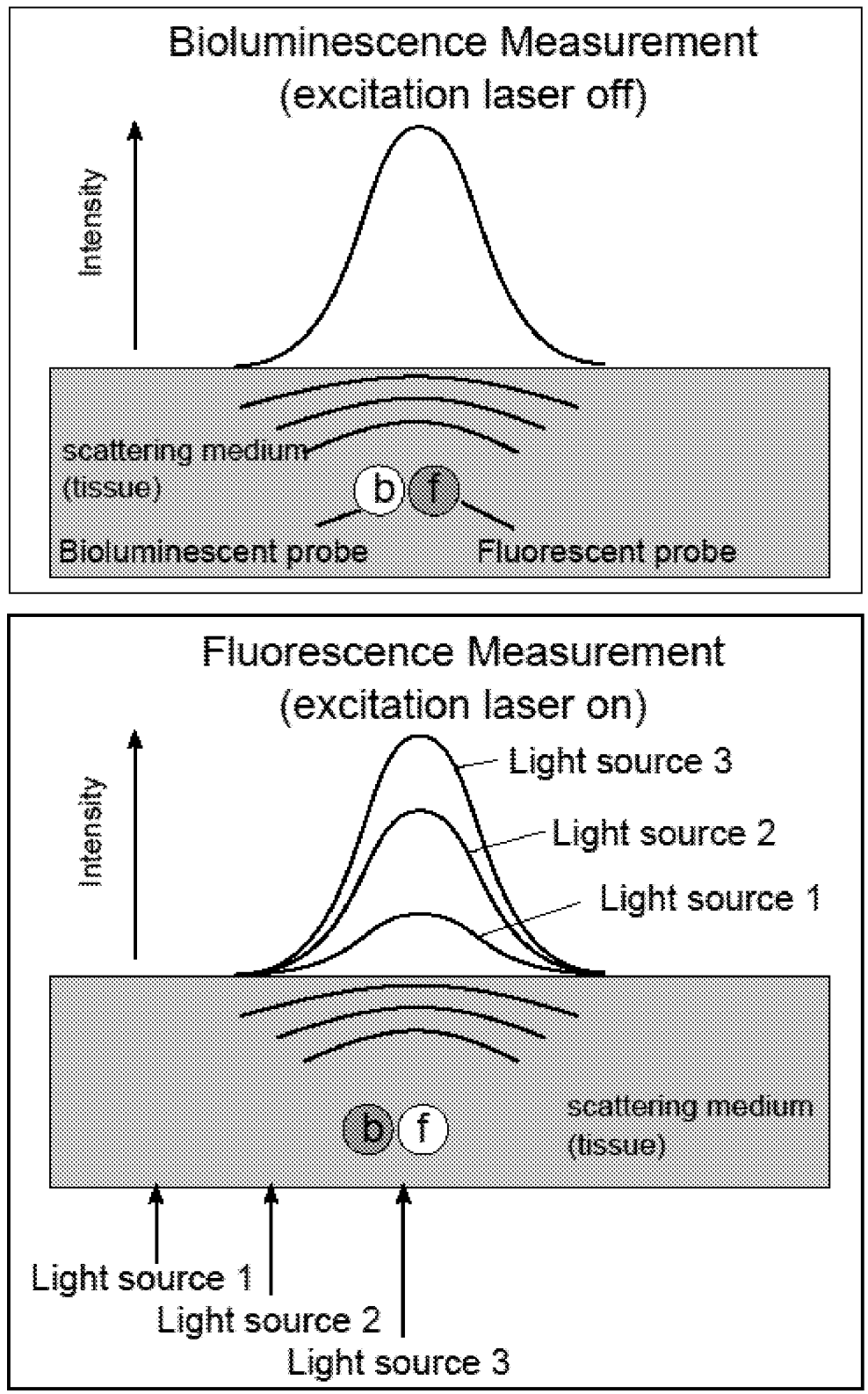
FIG. 1 is a schematic drawing depicting a comparison between an image generated by a bioluminescent source and one generated by a fluorescence source, the intensity of which can be modulated externally by changing the intensity of the excitation source. The shape of both signals should be, in the absence of auto-fluorescence, identical, with the only difference residing in their absolute intensity values.
Figure 2:
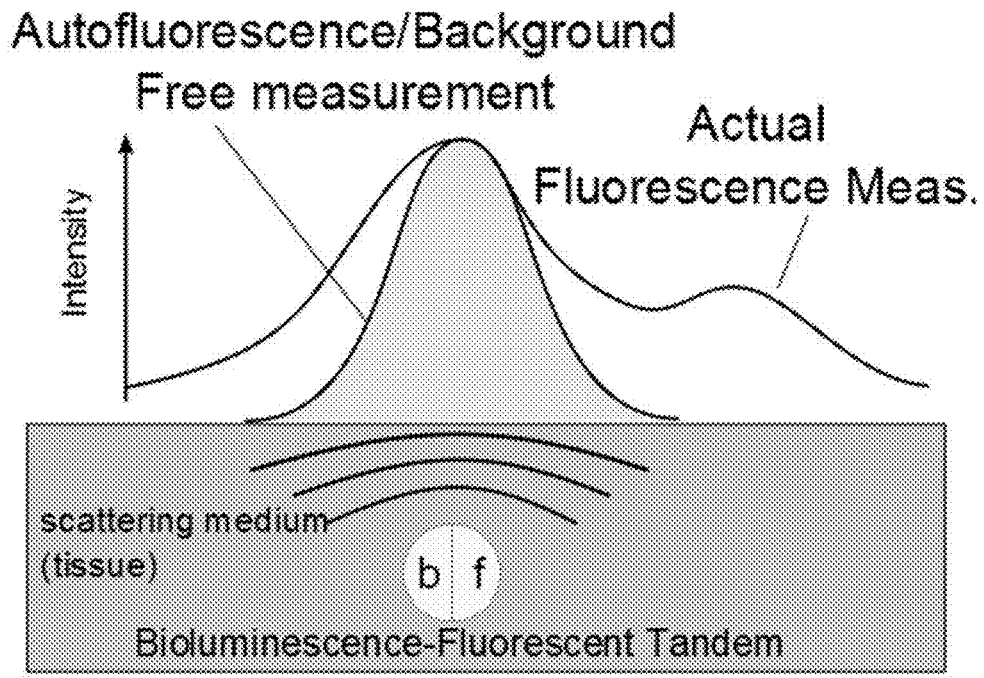
FIG. 2 is a schematic drawing depicting how the information due solely to the fluorophore can be identified with the bioluminescence profile when the fluorescence signal is degraded through contribution of auto-fluorescence and background signal.
Figure 2:
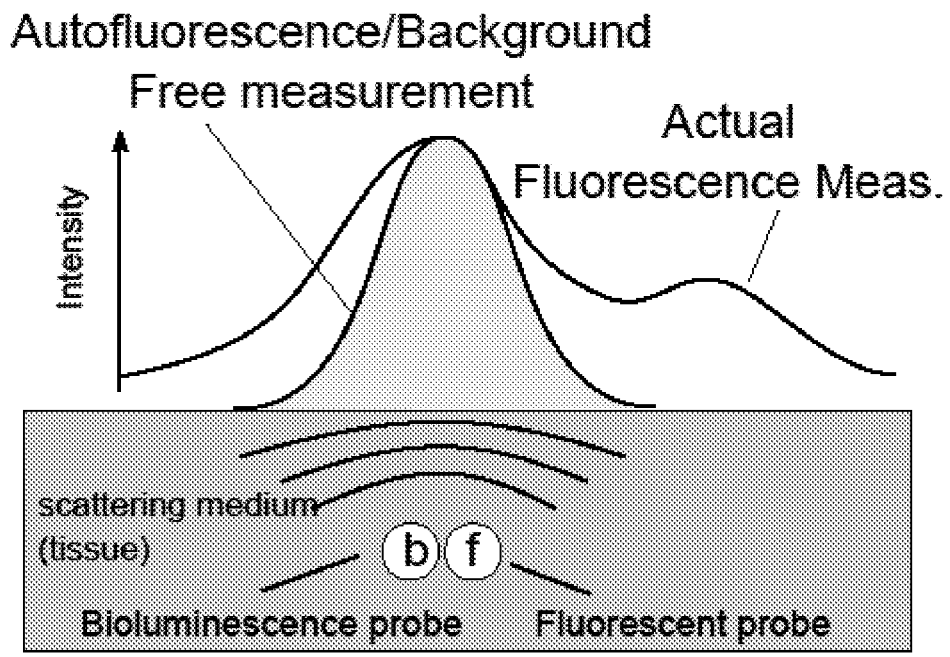
Figure 3:
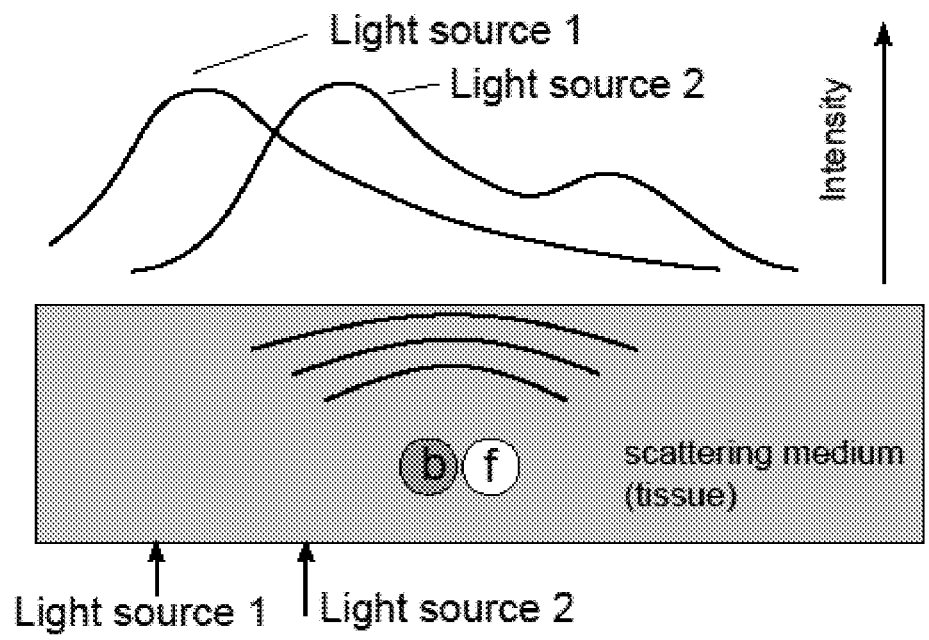
FIG. 3 is a schematic drawing depicting how the contribution of auto-fluorescence changes with the source position, while the fluorescence emission changes in intensity but not in distribution.
Figure 3:
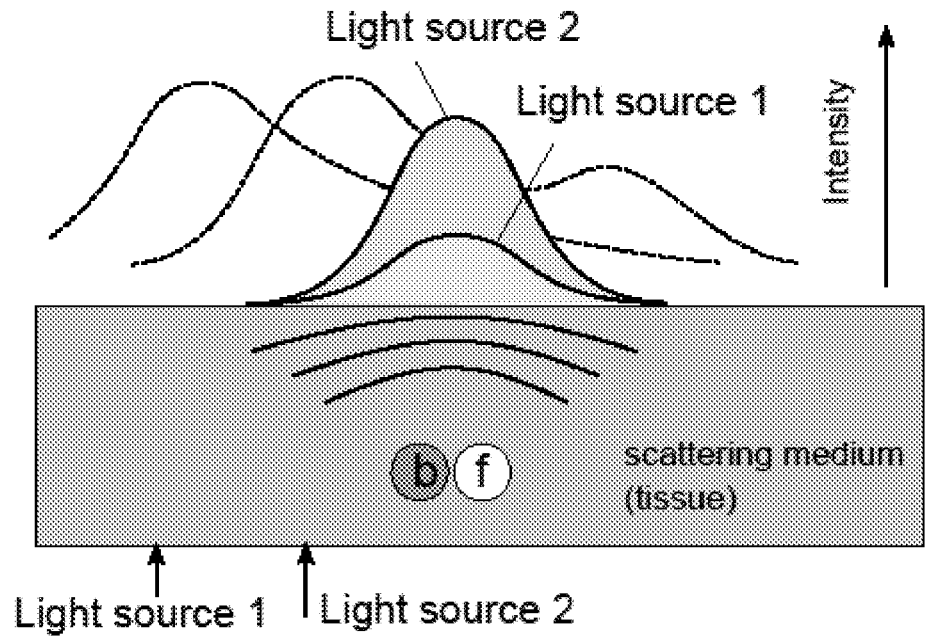
Figure 4:
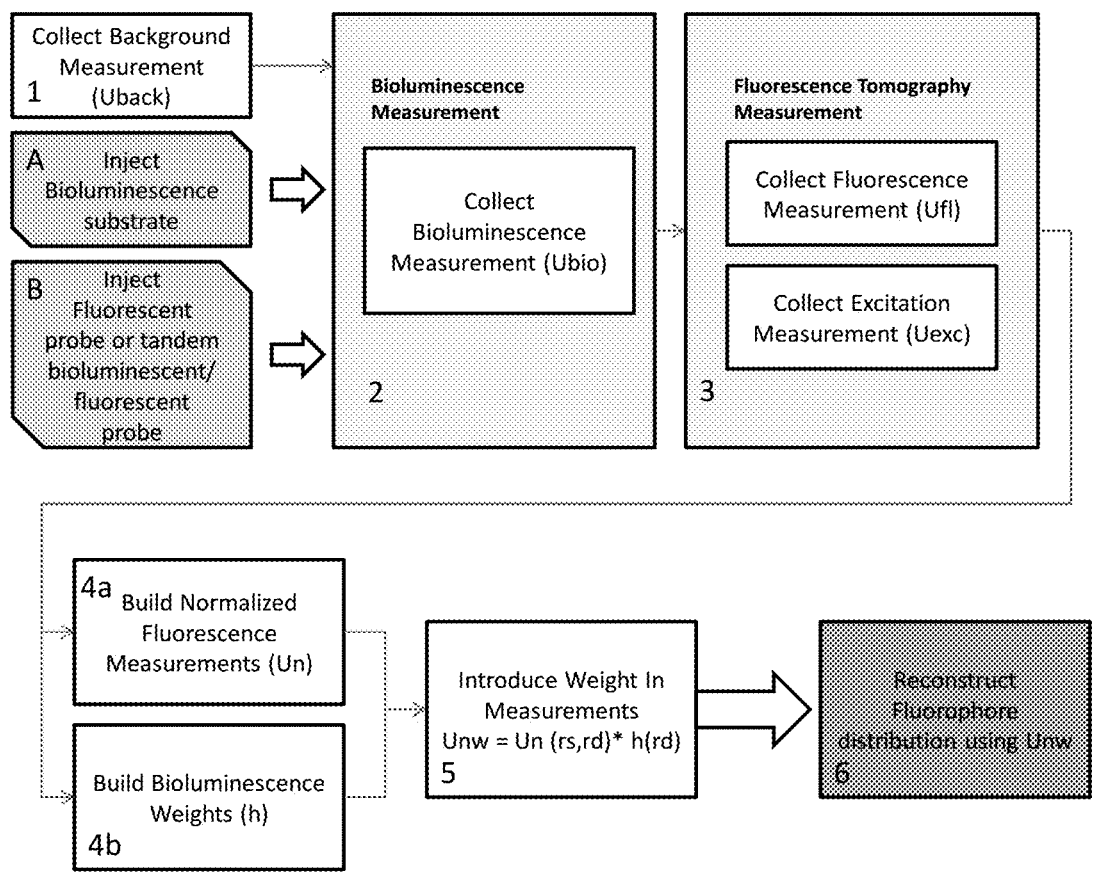
FIG. 4 is a block flow diagram depicting an example method of combining bioluminescence with normalized fluorescent measurements to obtain 3D images of fluorescent and/or bioluminescent sources, according to an illustrative embodiment of the invention.

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present invention that consist essentially of, or consist of, the recited components, and that there are processes and methods of the present invention that consist essentially of, or consist of, the recited processing steps.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are used herein to aid the reader and are not meant to limit the interpretation of the subject matter described.

As used herein, the term "image" is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout).

The term "tomographic image" may refer, for example, to an optical tomographic image, an x-ray tomographic image, a tomographic image generated by magnetic resonance, positron emission tomography (PET), magnetic resonance, (MR) single photon emission computed tomography (SPECT), and/or ultrasound, and any combination of these.

As used herein, the term "detector" includes any detector of electromagnetic radiation including, but not limited to, CCD camera, photomultiplier tubes, photodiodes, and avalanche photodiodes.

As used herein, the term "forward model" is understood to mean a physical model of light propagation in a given medium, for example, from a source to a detector.

Described herein are methods of measurement and analysis that combine information obtained from co-existent bioluminescence and fluorescent signals in diffuse media. These methods increase the accuracy of tomographic reconstructions in diffuse media and enhance the quantitative, three-dimensional structural, functional and molecular information obtained in in vivo imaging studies in small animals. This increase in accuracy is obtained by reducing the ill-posedness of bioluminescent imaging in order to obtain three-dimensional (3D) reconstructions from measurements of bioluminescence signals with the aid of fluorescence.

The bioluminescent signal and the probe-specific fluorescent signal in the absence of a background signal should be equivalent in morphology but not in intensity. It is the intensity of the fluorescence emission that provides the 3D information needed for the reconstruction, while the bioluminescence emission provides the background-free spatial signal distribution. By combining detection of both bioluminescence and fluorescence, it is possible to retrieve 3D information of fluorescent probes with the superior signal-to-noise ratio of bioluminescence due to the lack of background signal. In some embodiments, this invention further enables the use of analytical tools to combine the information obtained by bioluminescence and fluorescence measurements, resulting in improved feasibility of the imaging reconstructions from both types of light sources. These tools will provide 3D information to in vivo animal optical imaging setups through the use of normalized fluorescence measurements, while simultaneously providing auto-fluorescence-free measurements with the aid of bioluminescence.

One of the main analytical aspects when imaging diffuse media is the feasibility of simultaneously recovering information on the position, concentration, and distribution (or size) of a collection of light-emitting reporters (i.e., fluorescent or bioluminescent). In the case of a single excitation source or in its absence, as in the case of bioluminescence, there is an infinite combination of concentration, position, and size that will yield exactly the same measurement, which results in an ill-posed problem. The nature of this ill-posedness is fundamentally represented by the way information is lost during light propagation, as indicated by the transfer function, a function which relates the spatial distribution of intensity in Fourier space for the spatial frequencies K at a plane z' with the spatial distribution of intensity at another plane z:

$$H(K,z-z')=\exp(iq(K)|z-z'|) \qquad (1)$$

One way of reducing the ill-posedness of the problem is to change the intensity of the emission in a controlled manner, so that a spatial dependence is introduced. In the case of fluorescence, this can be done directly through the excitation source, $U_{exc}(r)$:

$$S(r)=\sigma_{abs}[C(r)]\Phi(\lambda_{em})U_{exc}(r) \qquad (2)$$

where $\sigma_{abs}$ represents the absorption cross-section of the fluorophore, $[C(r)]$ its concentration, $\Phi(\lambda_{em})$ its quantum yield, and $U_{exc}(r)$ the spatial distribution of excitation intensity. However, this may not be done for bioluminescence. Since a spatial dependence cannot be introduced on the emission of a bioluminescent reaction, the problem of recovering the position, concentration, or size of a bioluminescent probe will remain extremely ill-posed. This is a major drawback of bioluminescence.

In certain embodiments, methods described herein use the information obtained from coexistent bioluminescent and fluorescent tomographic signals co-localized at distances similar to or shorter than the scattering mean free path lsc. This leads to two important consequences. First, it allows the use of the spatial dependence introduced by the fluorescent excitation source to reduce the ill-posedness of the bioluminescent imaging. This has a direct impact in the recovery of bioluminescent probe spatial position and size, allowing a 3D reconstruction of the bioluminescent data obtained with the aid of fluorescent measurements. Second, this method allows the use of the high specificity of the bioluminescent signal to improve the accuracy of the tomographic reconstructions of the co-localized fluorescent signal, by providing information that will allow the discrimination of specific fluorescent signal from background or auto-fluorescence signal. This increases and improves the resolution, quantification, and most importantly, the sensitivity of fluorescence tomography.

The methods can be used, for example, where a tandem bioluminescence-fluorescence probe, or single or multiple co-localized bioluminescence reporter(s) and fluorescence probe(s) are used in the presence or absence of background auto-fluorescence or non-specific signal (such as excitation light leaking through the emission filters). Three examples of the approaches that can be used to combine the bioluminescence and fluorescence measurements are presented below, showcasing the feasibility of the method, but not limiting it to these approaches. A fourth example below describes an approach for acquiring the data that are used in the other examples, but does not limit the application to this approach.

Bioluminescence Weighted Fluorescence Data

As a first approach, a weight is introduced on fluorescence measurements by assuming that for each source position $r_s$ and detector $r_d$ represented by $U^{fl}(r_s,r_d)$, there is a measured distribution of bioluminescence $U^{bio}(r_d)$ (there is only a dependence on the detector in the case of bioluminescence). In this case, an example approach would be to determine the weight as:

$$h(r_d) = \frac{U^{bio}(r_d)}{\text{mean }\{U^{bio}(r_d)\}} \quad (3)$$

which would ensure that the weights are within the [0,1] range. The fluorescence measurements to be used for the reconstruction would be as follows:

$$U_w^{fl}(r_s,r_d)=U^{fl}(r_s,r_d)h(r_d) \quad (4)$$

There are a variety of ways of choosing the weight h. Another approach is to set a threshold in the measurement, so that h is defined as:

$$h(r_d, \text{thresh}) = \frac{U^{bio}(r_d)H(U^{bio}(r_d) > \text{thresh})}{\text{mean }\{U^{bio}(r_d)\}} \quad (5)$$

where H is the Heavyside function, which would yield 1 for values of the measurement above the threshold. This threshold will propagate to all fluorescence measurements, in which case the actual values used for the fluorescence reconstruction do not depend on the fluorescence signal measured but rather on the case of having actual bioluminescent (and therefore noise-free) signal or not. Once the weighted fluorescence measurement is defined, the regular reconstruction method is then performed, first normalizing the weighted fluorescence by the excitation, $U^{exc}(r_s,r_d)$:

$$U_{nw}(r_s, r_d) = \frac{U_w^{fl}(r_s, r_d)}{U^{exc}(r_s, r_d)} = \frac{U^{fl}(r_s, r_d)}{U^{exc}(r_s, r_d)}h(r_d) \quad (6)$$

This weighted normalized fluorescence can be used to recover the noise-free (or specific) fluorophore distribution, F(r) by inverting the equation:

$$U_{nw}(r_s,r_d)=\int_V W(r_s,r',r_d)F(r')dr' \quad (7)$$

where W is a function which represents the expected contribution of each point of the tissue volume V to the measurement at $r_d$ for a source distribution centered at $r_s$ and is usually termed the weight function. Both $r_s$ and $r_d$ may be located either on the surface or very close to it. The above equation may be discretized and solved as a system of equations since there is a discreet number of sources and detectors:

$$[F]_j=\{[W]_j^{sd}\}^{-1}[U_{nw}]_{sd} \quad (8)$$

Depending on the choice for the weight function, information on the inhomogeneities of the volume V may be included, in which case the above equation is non-linear, or the system of equations may be linearized, arriving at the Born Approximation.

Figure 5:
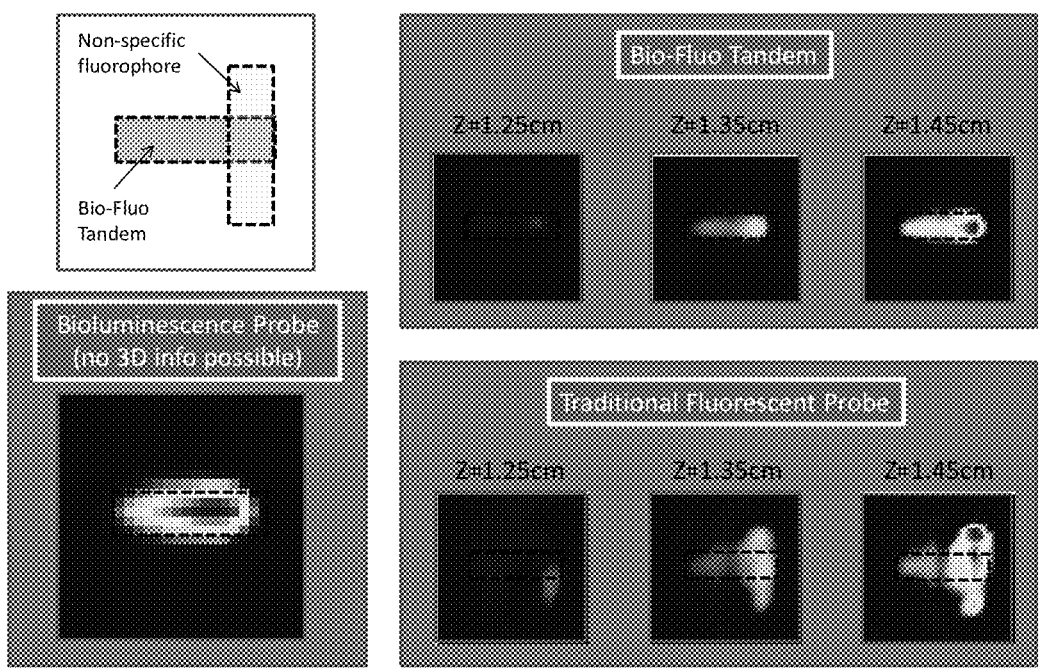
FIG. 5 shows the results of a simulation of the combination of bioluminescence with normalized fluorescent measurements to obtain accurate 3D images of fluorescent sources in the presence of non-specific background fluorescent signal, according to an illustrative embodiment of the invention.

An application of this example to simulated data, using a tandem bioluminescent and fluorescent construct in the presence of non-specific fluorescent background, is illustrated in FIG. 5.

Bioluminescence Weighted Fluorescence Data and Weight Matrix

In the previous example, consideration of the emission spectra of the bioluminescent reporters and the fluorescent probes was not introduced. In the specific case when both emit at different ranges of the spectrum, the actual emission profiles of both would be different. Introducing the weight due to the bioluminescence carries with it an assumption that both fluorescent and bioluminescent spectra are equivalent. In order to make this assumption more general, and actually independent of the bioluminescence spectra altogether, an accurate approach is to weight both the fluorescence and the weight matrix in the following manner:

$$U_{nw}(r_s,r_d)=h(r_d)\int_V W(r_s,r',r_d)F(r')dr' \quad (9)$$

In mathematical terms, this would give the same result as when the weight h is not used, with the significant difference that this weight makes zero those contributions which are not solely due to the specific probe. When inverting the system of equations:

$$[F]_j=\{[Wh]_j^{sd}\}^{-1}[U_{nw}]_{sd} \quad (10)$$

Those measurements which are not included in the weight function h are therefore not being used. In some embodiments, this approach yields quantitative data, regardless of the choice of h, as long as it is based on the bioluminescence measurement and this measurement is non-zero.

Fluorescence Weighted Bioluminescence Reconstruction

Because the basis of the recovery of a 3D distribution is based on the ability to modulate the light emission by introducing a spatial dependence, this light emission modulation may be introduced into the bioluminescence measurement by making use of the fluorescence measurements. To that end, one approach would be to measure the average normalized fluorescence emitted, weighted by the bioluminescence measurement for each source, that is:

$$I_w^{bio}(r_i) = \frac{\Sigma_j^{N_d}\left\{\left|\frac{U^{fl}(r_i, r_j)}{U^{exc}(r_i, r_j)}\right|U^{bio}(r_j)\right\}}{\text{mean }\{U^{bio}(r_j)\}} \quad (11)$$

where $N_d$ is the number of detectors. In doing the above, a fixed intensity distribution is determined, given by the bioluminescence image, and an intensity modulated by the excitation source given by $I_w^{bio}(r_i)$. As in the case of fluorescence, the 3D distribution of bioluminescence may now be recovered by:

$$U_w^{bio}(r_s,r_d)=U^{bio}(r_d)I_w^{bio}(r_s)=\int_V W(r_s,r',r_d)B(r')dr' \quad (12)$$

where now B represents the spatial distribution of substrate plus enzyme concentration of the bioluminescent reaction, and W is as defined for the fluorescence tomography case. Following the previous example, inverting the system of equations:

$$[B]_j=\{[W]_j^{sd}\}^{-1}[U_w^{bio}]_{sd} \quad (13)$$

Experiment Design and Acquisition of Data

In the previous three examples, an assumption is made that measurements are acquired of the bioluminescence signal as well as of the fluorescence excitation light source and the fluorescence signal. This example describes how these data may be acquired.

The first step is the preparation of the animal for imaging. The bioluminescent reporter and fluorescent probe is introduced into the animal, either by injection of a combined bioluminescent and fluorescent probe, by injection of separate bioluminescent and fluorescent probes, and/or by injection of a fluorescent probe into an animal model that already contains bioluminescent cells, e.g. luciferase-expressing transgenic cells. In any of these cases, a bioluminescence substrate, e.g. luciferin, is also injected at a time appropriate to enable both fluorescence and bioluminescence imaging sequentially. Because the pharmacokinetics (PK) of the probes and substrate may be different, these injections may need to be performed at different times.

After acquiring a noise image, the bioluminescence image is acquired, as are images at the excitation and fluorescence emission wavelengths using each light source. As an alternative to the bioluminescence image, a fluorescence image without an external light source could be acquired, with the fluorescent emission produced by means of radiative transfer from the bioluminescent emitters to the fluorescent acceptors. Bioluminescent stimulation of fluorescence by radiative transfer has been described using the acronym FUEL by Dragavon et al. (2010) Proc. of SPIE Vol. 7902, in an in vitro context. This approach has the dual advantages that the spectral mismatch described in the second example above is eliminated and the measured fluorescence would be limited to that stimulated directly by the bioluminescent reporter.

Finally, the fluorescence images would be normalized by their corresponding excitation images as described, for example, in U.S. Pat. Nos. 6,615,063; 7,383,076.

In certain embodiments, the methods of the present invention are useful with optical imaging modalities and measurement techniques including, but not limited to: endoscopy; fluorescence endoscopy; luminescence imaging; bioluminescence tomography, time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

Commercially available systems that can be used to employ the systems and methods described herein include, but are not limited to, the following: eXplore Optix™, Optix® and SoftScan® (ART—Advanced Research Technologies, Canada), NightOWL® II LB (Berthold Technologies, Germany), NanoSPECT™, NanoPET/CT™ and HiSPECT® (Bioscan, Washington, DC), Photon Imager™, Beta Imager™, Micro Imager, Gamma Imager (Biospace Lab, France), Maestro® FLEX and Nuance® FLEX (Cambridge Research and Instrumentation—Cri®, Woburn, MA), LightSpeed™, BrightSpeed™ and MR Signa® Series, eXplore Series, Triumph™ (GE® Healthcare, United Kingdom), Kodak® In-Vivo Imaging FX Systems, Kodak® In-Vivo Multispectral Imaging FX Systems and Kodak® Image Station 4000 series (KODAK® and Carestream®, Rochester, NY), Aquacosmos® (Hamamatsu, Japan), CTLM® and LILA Imaging Systems (Imaging Diagnostic Systems—IMDS, Plantation, FL), Odyssey® Infrared Imaging System, Pearl® Imager (LI-COR, Lincoln, NE), IMRIS® Neuro System (IMRIS®, Canada), Cellvizio® (Mauna Kea Technologies, France), SPY® and SPY®-TMR Systems, HELIOS™, LUNA™, PINPOINT®, and OPTTX® Imaging Systems (Novadaq, Canada), DYNOT Imaging System (NIRx, Glen Head, New York), OV100 and IV100 (Olympus Corporation, Japan), Lumazone® (Photometrics, Tucson, AZ), and IVIS® Systems, IVIS® 3D, IVIS® Kinetics, IVIS® Spectrum and IVIS® Lumina (Xenogen®, Alamaeda, CA and Caliper® Life Sciences, Hopkinton, MA), iBox® (UVP, Upland, Ca), and VisEn FMT-1, VisEn FMT 1500™, and VisEn FMT2500™ LX (VisEn™ Medical, Bedford, MA).

Figure 6:
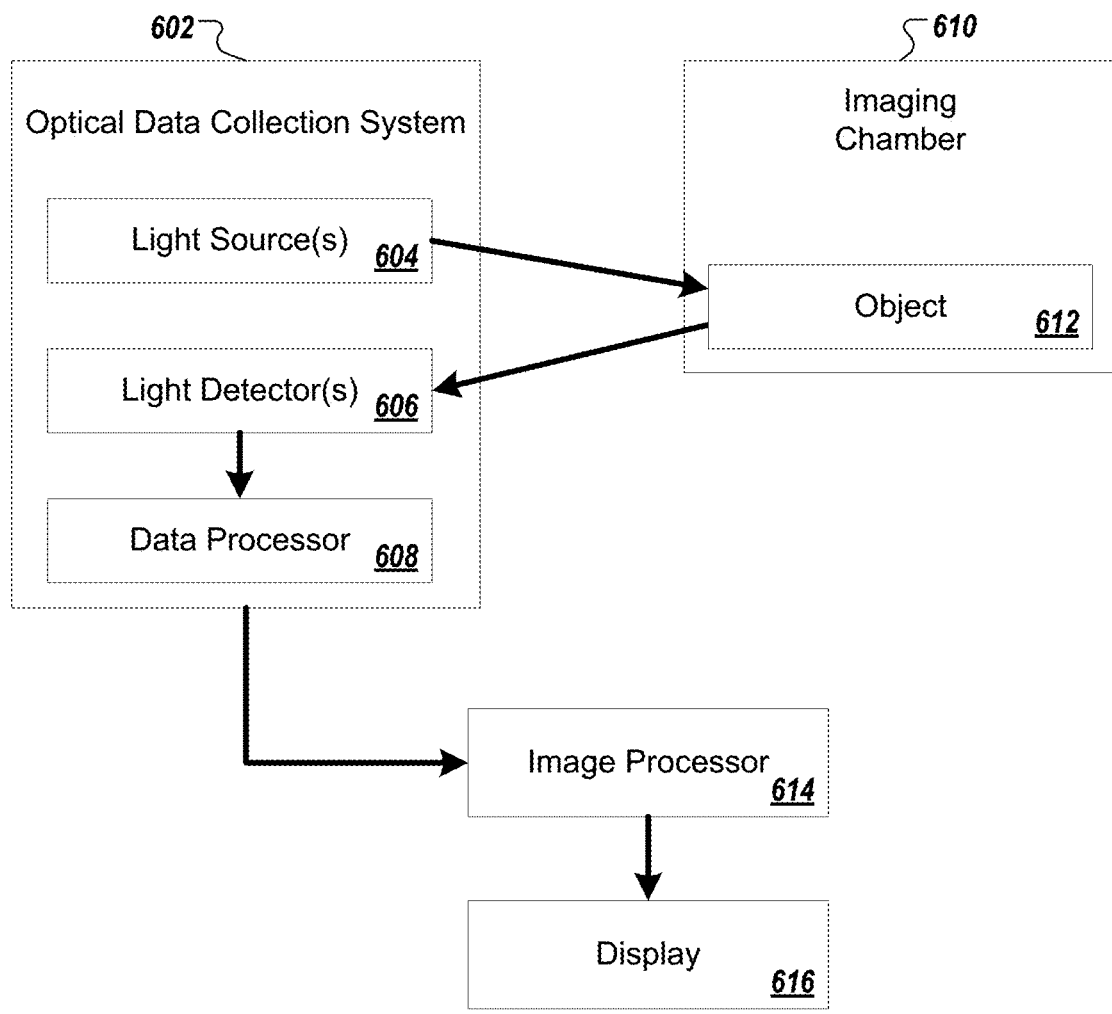
FIG. 6 shows a schematic of a diffuse optical tomography imaging system that may be used in various embodiments described herein.

FIG. 6 shows a schematic of a diffuse optical tomography imaging system 600 that may be used in various embodiments described herein. The optical data collection system 602 includes one or more light sources 604, for example, a laser providing near infrared excitation light at a given wavelength, e.g., in the 650 nm to 900 nm range. Multiple wavelengths of excitation light may be used. The light source(s) 604 illuminate the object 612 within the imaging chamber 610, and light from the object is detected by one or more light detector(s) 606. The light detector(s) 606 may be, for example, a CCD camera, e.g., a time-gated intensified CCD camera (iCCD).

The imaging chamber 610 houses the object 612 being imaged. The imaging chamber may be designed to allow direct optical contact between the object 612 and the light source(s) 604 and detector(s) 606, or there may be free space (e.g., air) between the object 612 and the light source(s) 604 and/or detector(s) 606.

A data processor 608 can be part of the optical data collection system 602 to pre-process or process image data, and/or a separate image processor 614 can be used to process image data. Data corresponding to the excitation light transmitted through the object 612, i.e., the transilluminating excitation light, can be processed along with the fluorescent light and/or bioluminescent light images for improved accuracy. Background light can be corrected for and calibration performed for repeatability and accuracy of imaging results. A forward problem is established and tomographic reconstruction performed to provide the tomographic image. Per methods described herein, the detected bioluminescent light, detected fluorescent light, and/or detected excitation light can be processed to provide a resulting tomographic image. The resulting tomographic image can be displayed on a standard display 616. Optical filters may be used.

Systems of the invention may include a computer which executes software that controls the operation of one or more instruments, and/or that processes data obtained by the system. The software may include one or more modules recorded on machine-readable media such as magnetic disks, magnetic tape, CD-ROM, and semiconductor memory, for example. The machine-readable medium may be resident within the computer or can be connected to the computer by a communication link (e.g., access via internet link). However, in alternative embodiments, one can substitute computer instructions in the form of hardwired logic for software, or one can substitute firmware (i.e., computer instructions recorded on devices such as PROMs, EPROMS, EEPROMs, or the like) for software. The term machine-readable instructions as used herein is intended to encompass software, hardwired logic, firmware, object code and the like.

The computer is preferably a general purpose computer. The computer can be, for example, an embedded computer, a personal computer such as a laptop or desktop computer, or another type of computer, that is capable of running the software, issuing suitable control commands, and/or recording information in real-time. The computer may include a display for reporting information to an operator of the instrument (e.g., displaying a tomographic image), a keyboard for enabling the operator to enter information and commands, and/or a printer for providing a print-out, or permanent record, of measurements made by the system and for printing diagnostic results, for example, for inclusion in the chart of a patient. In certain embodiments, some commands entered at the keyboard enable a user to perform certain data processing tasks. In certain embodiments, data acquisition and data processing are automated and require little or no user input after initializing the system.

In certain embodiments, the invention features an in vivo imaging method for selectively imaging a subject containing two or more imaging probes simultaneously, wherein two or more imaging probes are administered to a subject, either at the same time or sequentially. The imaging probes can be any combination of optical or other imaging agents. A single imaging agent may serve as both an optical and other imaging modality agent, e.g., dual imaging agent. The method therefore allows the recording of multiple biological processes, functions or targets. The methods of the invention can be used to determine a number of indicia, including tracking the localization of the imaging probes in the subject over time or assessing changes or alterations in the metabolism and/or excretion of the imaging probes in the subject over time. The methods can also be used to follow therapy for such diseases by imaging molecular events and biological pathways modulated by such therapy, including but not limited to determining efficacy, optimal timing, optimal dosing levels (including for individual patients or test subjects), pharmacodynamic parameters, and synergistic effects of combinations of therapy.

In certain embodiments, this invention can be used with other imaging approaches such as the use of devices including but not limited to various scopes (microscopes, endoscopes), catheters and optical imaging equipment, for example computer based hardware for tomographic presentations.

Embodiments of the invention can be used, for example, to help a physician, surgeon, or other medical personnel or researcher to identify and characterize areas of disease, such as arthritis, cancers, metastases or vulnerable or unstable plaque, to distinguish diseased and normal tissue, such as detecting tumor margins that are difficult to detect.

In certain embodiments, the methods of the invention can be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies. The methods of the invention can also be used in prognosis of a disease or disease condition. With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone, including metastases), cardiovascular disease (for example, atherosclerosis and inflammatory conditions of blood vessels, ischemia, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants). The methods of the invention can therefore be used, for example, to determine the presence of tumor cells and localization and metastases of tumor cells, the presence and localization of inflammation, including the presence of activated macrophages, for instance in atherosclerosis or arthritis, the presence and localization of vascular disease including areas at risk for acute occlusion (e.g., vulnerable plaques) in coronary and peripheral arteries, regions of expanding aneurysms, unstable plaque in carotid arteries, and ischemic areas, and stent thrombosis. The methods and compositions of the invention can also be used in identification and evaluation of cell death, injury, apoptosis, necrosis, hypoxia and angiogenesis. The methods and compositions of the invention can also be used in for monitoring trafficking and localization of certain cell types, including T-cells, tumor cells, immune cells, stem cells, and other cell types. In particular, this method may be used to monitor cell based therapies. The methods and compositions of the invention can also be used as part of photodynamic therapy, including imaging, photoactivation and therapy monitoring.

In certain embodiments, the systems and methods described herein can be used to image endogenous fluorescence in a subject. For example, a gene encoding a fluorescent protein, such as green, red or infrared fluorescent protein, can be included adjacent to a gene of interest that is to be expressed in an animal or human subject using standard gene therapy and transgenic techniques. The expression of the gene of interest can be determined indirectly by imaging the fluorescent protein. If this protein is expressed, then the gene of interest has also been expressed. Fluorescence properties of endogenous fluorescent proteins are described in Giepmans et al., *Science,* 312: 217-224, 2006; Shaner et al., *Nature Methods* 2:905-909, 2005; and Zhang et al., *Nat. Rev. Mol. Biol.* 3: 906-918, 2002; Ai et al., *Biochemistry* 46:5904-5910, 2007; Shaner et al., *Nat. Biotech* 22:1567-1572, 2004; Campbell et al., *Proc. Nat. Acad. Sci.* 99:7877-7882, 2002; Heikal et al. *Proc. Nat. Acad. Sci.* 97:11996-12001, 2000; Baird et al., *Proc. Nat. Acad. Sci.* 97:11984-11989, 2000; Tsien, *Ann. Rev. Biochem.* 67:509-44, 1998; Heim et al., *Curr. Biol.* 6:178-182, 1996; Cubitt et al., *Trends Biochem Sci.* 11:448-455, 1995; Heim et al., *Proc. Nat. Acad. Sci* 91:12501-12504, 1994; the relevant text incorporated by reference herein.

In certain embodiments, the systems and methods described herein can be used with systems and methods described in U.S. Pat. Nos. 6,615,063; 7,383,076; and 8,190,241, which relate to extracting quantitative, three-dimensional molecular information from living mammals and patients using fluorochromes and optical tomographic imaging methods. These patents describe the use of detected fluorescent images together with images of transilluminating excitation light to obtain a more accurate tomographic image of a target region.

In certain embodiments, the systems and methods described herein can be used with systems and methods described in U.S. Patent Application Publication No. US 2007/0238957, which relates to the use of X-ray data to account for different tissue types and densities in diffuse optical tomography.

In certain embodiments, the systems and methods described herein can be used with systems and methods described in U.S. Patent Application Publication No. 2005/0283071, U.S. Pat. No. 8,170,651, and U.S. Patent Application Publication No. 2013/0114069, which relate to computational systems and methods for imaging volumes with arbitrary geometries in non-contact tomography.

In certain embodiments, the systems and methods described herein can be used with systems and methods described in U.S. Pat. No. 8,401,618, which relates to in vivo imaging systems and methods for tomographic imaging employing a hybrid approach for fast reconstruction. In this hybrid approach, one or more subsets of large tomographic datasets are selected in frequency space (e.g., Fourier space) while one or more subsets are maintained in real space, then the weight matrix is inverted to obtain the tomographic representation of a region of interest within the subject in real space. This achieves fast computational times while maintaining good tomographic reconstruction performance.

In certain embodiments, the systems and methods described herein can be used with systems and methods described in U.S. Pat. No. 8,401,619, which relates to in vivo imaging systems and methods employing a virtual index matching technique.

Imaging Probes (Fluorescent Species)

The imaging system and method can be used with a number of different fluorescent imaging probes (or, as in embodiments using a tandem bioluminescent reporter/fluorescent probe, the fluorescent species thereof), for example, (1) probes that become activated after target contact (e.g., binding or interaction) (Weissleder et al., *Nature Biotech.*, 17:375-378, 1999; Bremer et al., *Nature Med.*, 7:743-748, 2001; Campo et al., *Photochem. Photobiol.* 83:958-965, 2007); (2) wavelength shifting beacons (Tyagi et al., *Nat. Biotechnol.*, 18:1191-1196, 2000); (3) multicolor (e.g., fluorescent) probes (Tyagi et al., *Nat. Biotechnol.*, 16:49-53, 1998); (4) probes that have high binding affinity to targets, e.g., that remain within a target region while non-specific probes are cleared from the body (Achilefu et al., *Invest. Radiol.*, 35:479-485, 2000; Becker et al., *Nature Biotech.* 19:327-331, 2001; Bujai et al., *J. Biomed. Opt.* 6:122-133, 2001; Ballou et al. *Biotechnol. Prog.* 13:649-658, 1997; and Neri et al., *Nature Biotech.* 15:1271-1275, 1997); (5) quantum dot or nanoparticle-based imaging probes, including multivalent imaging probes, and fluorescent quantum dots such as amine T2 MP EviTags® (Evident Technologies) or Qdot® Nanocrystals (Invitrogen™); (6) non-specific imaging probes e.g., indocyanine green, AngioSense® (VisEn Medical); (7) labeled cells (e.g., such as cells labeled using exogenous fluorophores such as VivoTag™ 680, nanoparticles, or quantum dots, or by genetically manipulating cells to express fluorescent or luminescent proteins such as green or red fluorescent protein; and/or (8) X-ray, MR, ultrasound, PET or SPECT contrast agents such as gadolinium, metal oxide nanoparticles, X-ray contrast agents including iodine based imaging agents, or radioisotopic form of metals such as copper, gallium, indium, technetium, yttrium, and lutetium including, without limitation, 99m-Tc, 111-In, 64-Cu, 67-Ga, 186-Re, 188-Re, 153-Sm, 177-Lu, and 67-Cu. The relevant text of the above-referenced documents are incorporated by reference herein. Another group of suitable imaging probes are lanthanide metal-ligand probes. Fluorescent lanthanide metals include europium and terbium. Fluorescence properties of lanthanides are described in Lackowicz, 1999, Principles of Fluorescence Spectroscopy, $2^{nd}$ Ed., Kluwar Academic, New York, the relevant text incorporated by reference herein. In the methods of this invention, the imaging probes can be administered systemically or locally by injecting an imaging probe or by topical or other local administration routes, such as "spraying". Furthermore, imaging probes used in the application of this invention can be conjugated to molecules capable of eliciting photodynamic therapy. These include, but are not limited to, Photofrin, Lutrin, Antrin, aminolevulinic acid, hypericin, benzoporphyrin derivative, and select porphyrins.

In general, fluorescent quantum dots used in the practice of this invention are nanocrystals containing several atoms of a semiconductor material (including but not limited to those containing cadmium and selenium, sulfide, or tellurium; zinc sulfide, indium-antimony, lead selenide, gallium arsenide, and silica or ormosil), which have been coated with zinc sulfide to improve the properties of the fluorescent agents.

In particular, molecular imaging probes are a preferred type of imaging probe. A molecular imaging probe is a probe that is targeted to a biomarker, molecular structure or biomolecule, such as a cell-surface receptor or antigen, an enzyme within a cell, or a specific nucleic acid, e.g., DNA, to which the probe hybridizes. Biomolecules that can be targeted by imaging probes include, for example, antibodies, proteins, glycoproteins, cell receptors, neurotransmitters, integrins, growth factors, cytokines, lymphokines, lectins, selectins, toxins, carbohydrates, internalizing receptors, enzyme, proteases, viruses, microorganisms, and bacteria.

In certain embodiments, optical imaging probes have excitation and emission wavelengths in the red and near infrared spectrum in the range 550-1300 or 400-1300 nm or about 440 and about 1100 nm, between about 550 and about 800 nm, between about 600 and about 900 nm. Use of this portion of the electromagnetic spectrum maximizes tissue penetration and minimizes absorption by physiologically abundant absorbers such as hemoglobin (<650 nm) and water (>1200 nm). Optical imaging probes with excitation and emission wavelengths in other spectrums, such as the visible and ultraviolet light spectrum, can also be employed in the methods of the present invention. In particular, fluorophores such as certain carbocyanine or polymethine fluorescent fluorochromes or dyes can be used to construct optical imaging agents, e.g. U.S. Pat. No. 6,747,159 to Caputo et al. (2004); U.S. Pat. No. 6,448,008 to Caputo et al. (2002); U.S. Pat. No. 6,136,612 to Della Ciana et al. (2000); U.S. Pat. No. 4,981,977 to Southwick, et al. (1991); U.S. Pat. No. 5,268,486 to Waggoner et al. (1993); U.S. Pat. No. 5,569,587 to Waggoner (1996); U.S. Pat. No. 5,569,766 to Waggoner et al. (1996); U.S. Pat. No. 5,486,616 to Waggoner et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); U.S. Pat. No. 7,445,767 to Licha, et al. (2008); U.S. Pat. No. 6,534,041 to Licha et al. (2003); U.S. Pat. No. 7,547,721 to Miwa et al. (2009); U.S. Pat. No. 7,488,468 to Miwa et al. (2009); U.S. Pat. No. 7,473,415 to Kawakami et al. (2003); also WO 96/17628, EP 0 796 111 B1, EP 1 181 940 B1, EP 0 988 060 B1, WO 98/47538, WO 00/16810, EP 1 113 822 B1, WO 01/43781, EP 1 237 583 A1, WO 03/074091, EP 1 480 683

B1, WO 06/072580, EP 1 833 513 A1, EP 1 679 082 A1 WO 97/40104, WO 99/51702, WO 01/21624, and EP 1 065 250 A1; and Tetrahedron Letters 41, 9185-88 (2000).

Exemplary fluorochromes for optical imaging probes include, for example, the following: Cy5.5, Cy5, Cy7.5 and Cy7 (GE® Healthcare); AlexaFluor660, AlexaFluor680, AlexaFluor790, and AlexaFluor750 (Invitrogen); VivoTag™680, VivoTag™-5680, VivoTag™-S750 (VisEn Medical); Dy677, Dy682, Dy752 and Dy780 (Dyomics®); DyLight® 547, and/or DyLight® 647 (Pierce); HiLyte Fluor™ 647, HiLyte Fluor™ 680, and HiLyte Fluor™ 750 (AnaSpec®); IRDye® 800CW, IRDye® 800R5, and IRDye® 700DX (Li-Cor®); ADS780WS, ADS830WS, and ADS832WS (American Dye Source); XenoLight CF™ 680, XenoLight CF™ 750, XenoLight CF™ 770, and XenoLight DiR (Caliper® Life Sciences); and Kodak® X-SIGHT® 650, Kodak® X-SIGHT 691, Kodak® X-SIGHT 751 (Carestream® Health).

While the invention has been particularly shown and described with reference to specific preferred embodiments, it should be understood by those skilled in the art that various changes in form and detail may be made therein without departing from the spirit and scope of the invention as defined by the appended claims. The relevant teachings of all the references, patents and patent applications cited herein are incorporated herein by reference in their entirety.

What is claimed is:

1. A system for imaging a target region within a diffuse object, the system comprising:
   an excitation light source;
   an optical imaging apparatus configured to direct light from the excitation light source into the diffuse object at one or more of: (i) multiple locations and (ii) multiple angles;
   one or more detectors, the one or more detectors individually or collectively configured to at least one of detect or measure: (i) one or more of bioluminescent or chemiluminescent light emitted from the diffuse object by a bioluminescent reporter in the target region of the diffuse object, (ii) fluorescent light emitted by a fluorescent species in the target region of the diffuse object as a result of excitation by the light, and (iii) excitation light having been transmitted through the target region of the diffuse object or having been reflected from the target region of the diffuse object; and
   a processor configured to process data corresponding to the one or more of bioluminescent or chemiluminescent light, the fluorescent light, and the excitation light to provide an image of the target region within the diffuse object.

2. The system of claim 1, wherein the bioluminescent reporter is endogenous.

3. The system of claim 2, wherein the bioluminescent reporter is expressed within the diffuse object by a bioluminescent cell line.

4. The system of claim 1, wherein the bioluminescent reporter is exogenously administered.

5. The system of claim 1, further comprising a probe comprising the fluorescent species, wherein the fluorescent species is at least one of fluorescent or jointly fluorescent/bioluminescent,
   wherein the probe is administered to the diffuse object, and
   wherein at least some of the bioluminescent reporter is substantially co-located with at least some of the probe in the target region of the diffuse object.

6. The system of claim 5, wherein the bioluminescent reporter is also present in the diffuse object at one or more locations that are not substantially co-located with the probe.

7. The system of claim 1, further comprising a probe, wherein the probe is administered to the diffuse object, and
   wherein the probe comprises both the fluorescent species and the bioluminescent reporter in tandem with the fluorescent species.

8. The system of claim 1, wherein the diffuse object comprises living biological tissue.

9. The system of claim 1, wherein the diffuse object is located within a holder.

10. The system of claim 9, wherein the image of the target region is a tomographic image, and
    wherein a surface of the diffuse object is at least partially conformed by the holder such that the surface can be characterized by a continuous function, thereby facilitating tomographic reconstruction.

11. The system of claim 1, wherein the target region of the diffuse object is a three-dimensional target region, and
    wherein the processor is configured to provide a tomographic image that corresponds to the fluorescent species in the three-dimensional target region.

12. The system of claim 11, wherein the tomographic image indicates concentration of a probe as a function of position within the target region of the diffuse object.

13. The system of claim 1, wherein the target region of the diffuse object is a three-dimensional target region, and
    wherein the processor is configured to provide a tomographic image that corresponds to the bioluminescent reporter in the three-dimensional target region.

14. The system of claim 1, wherein the processor is further configured to:
    weight the data corresponding to the fluorescent light with the data corresponding to the one or more of bioluminescent or chemiluminescent light; and
    normalize the data corresponding to the fluorescent light with the data corresponding to the excitation light.

15. The system of claim 14, wherein the processor is further configured to:
    invert an associated weight matrix to obtain a tomographic image of the fluorescent species in the target region of the diffuse object.

16. The system of claim 1, wherein the processor is further configured to:
    weight the data corresponding to the fluorescent light with the data corresponding to the one or more of bioluminescent or chemiluminescent light;
    weight an associated weight matrix with the data corresponding to the one or more of bioluminescent or chemiluminescent light; and
    invert the associated weight matrix to obtain a tomographic image of the fluorescent species in the target region of the diffuse object.

17. The system of claim 1, wherein the processor is further configured to:
    weight the data corresponding to the one or more of bioluminescent or chemiluminescent light with the data corresponding to the fluorescent light normalized with the data corresponding to the excitation light; and
    invert an associated weight matrix to obtain a tomographic image of the bioluminescent reporter in the target region of the diffuse object.

18. The system of claim 1, wherein the one or more of bioluminescent or chemiluminescent light is detected by the one or more detectors at a time different than when the fluorescent light is detected by the one or more detectors.

19. One or more non-transitory computer-readable media storing computer readable instructions that, when executed, cause a system to process data corresponding to detected excitation light, detected bioluminescent and/or chemiluminescent light, and detected fluorescent light to provide an image of a target region within a diffuse object, by performing:

determining an amount of excitation light corresponding to the excitation light emitted, from an excitation light source, into the diffuse object at multiple locations and/or at multiple angles, wherein the detected excitation light corresponds to excitation light that has been either transmitted through the target region of the diffuse object or reflected from the target region of the diffuse object, determining an amount of bioluminescent and/or chemiluminescent light corresponding to the bioluminescent and/or chemiluminescent light emitted, from the diffuse object, by a bioluminescent reporter in the target region of the diffuse object, determining an amount of fluorescent light corresponding to the fluorescent light emitted, by a fluorescent species, in the target region of the diffuse object as a result of excitation by the excitation light.

20. An apparatus for reconstructing a tomographic representation of a probe within a target region of a diffuse object, the apparatus comprising:

one or more processors controlling operations of the apparatus; and a memory that stores computer readable instructions that, when executed by the one or more processors, configure the apparatus to:

(a) establish a forward model of excitation light propagation from an excitation light source to the probe within the target region of the diffuse object and of emission light propagation from the probe to a detector using (i) data corresponding to detected fluorescent light from the probe, (ii) data corresponding to detected excitation light having been transmitted through the target region of the diffuse object or having been reflected from the target region of the diffuse object, and (iii) data corresponding to detected bioluminescent light emitted from a bioluminescent reporter, wherein at least some of the bioluminescent reporter is substantially co-located with at least some of the fluorescent light from the probe in the target region of the diffuse object, and wherein the forward model is established as a weight matrix; and (b) invert the weight matrix to obtain the tomographic representation of the probe within the target region of the diffuse object.

* * * * *